Figure 1:
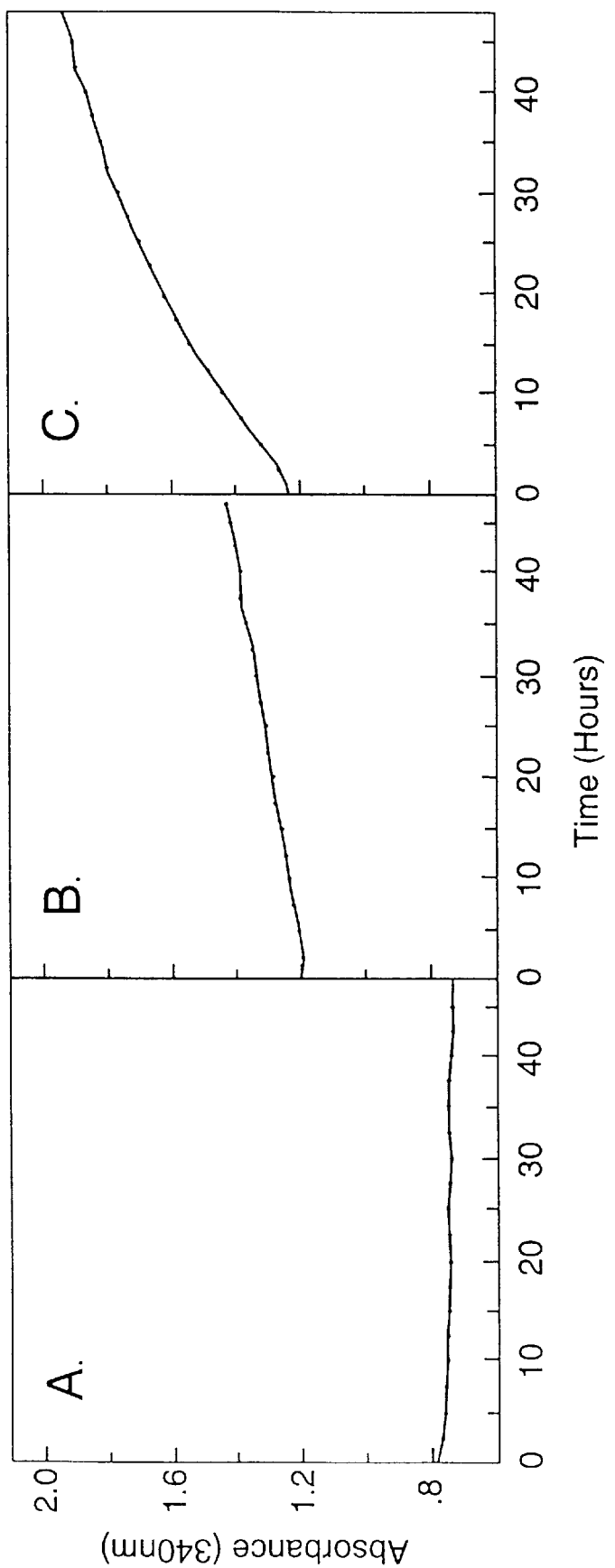

United States Patent [19]
De Giorgio et al.

[11] Patent Number: 5,804,402
[45] Date of Patent: Sep. 8, 1998

[54] REAGENT

[75] Inventors: Joseph De Giorgio; Wayne Jensen, both of Clayton, Australia

[73] Assignee: Trace Scientific Ltd., Clayton, Australia

[21] Appl. No.: 607,234

[22] Filed: Feb. 26, 1996

[30] Foreign Application Priority Data

Mar. 28, 1995 [AU] Australia .................. PN 2006

[51] Int. Cl.$^6$ .................. C12Q 1/54; C12Q 1/52; C12Q 1/32; G01N 33/53
[52] U.S. Cl. .................. 435/14; 435/16; 435/12; 435/26; 435/25; 435/4; 435/963
[58] Field of Search .................. 435/14, 16, 12, 435/26, 25, 4, 963

[56] References Cited

U.S. PATENT DOCUMENTS

| | | | |
|---|---|---|---|
| 3,956,069 | 5/1976 | Allain et al. | 435/14 |
| 4,153,511 | 5/1979 | Modrovich | 435/14 |
| 4,310,624 | 1/1982 | Modrovich | 435/14 |
| 4,394,449 | 7/1983 | Modrovich | 435/14 |
| 5,116,728 | 5/1992 | Crowther et al. | 435/14 |

FOREIGN PATENT DOCUMENTS

| | | |
|---|---|---|
| B-49 276/79 | 2/1980 | Australia . |
| B-61906/90 | 2/1991 | Australia . |
| 34213 | 8/1980 | European Pat. Off. . |
| 603 831 A1 | 6/1994 | European Pat. Off. . |
| WO 95/07999 | 3/1995 | WIPO . |

*Primary Examiner*—Louise N. Leary
*Attorney, Agent, or Firm*—Greenlee, Winner and Sullivan, PC

[57] ABSTRACT

This invention relates to a reagent for enzymatic determination of an analyte concentration in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent. Also disclosed is an improvement in an enzymatic method of determination of an analyte concentration in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent. Also disclosed are reagents for the determination of aspartate aminotransferase, alanine aminotransferase, ammonia and urea.

36 Claims, 2 Drawing Sheets

NADH Regeneration Studies for the Ammonia Reagent

REAGENT

This invention relates to reagents used in enzymatic methods of determining the concentration of analytes in a sample body fluid. In particular, this invention relates to reagents used in methods wherein the quantity of an oxidized coenzyme in the reacted sample corresponds directly to the concentration of analyte present in the sample. The invention also relates to improved methods for carrying out the determination of the analyte concentration.

Analytes that can be determined by the reagents of the invention include transaminases, ammonia, urea, lactate dehydrogenase, triglycerides and salicylate.

Aspartate aminotransferase is an enzyme found in high levels in the heart, the liver, in red blood cells and in skeletal muscle. It catalyzes the following reaction:

$$\text{aspartate} + \text{2-oxoglutarate} \rightleftharpoons \text{oxaloacetate} + \text{glutamate}$$

Increases in serum levels of aspartate aminotransferase are found in many liver diseases where there is liver cell destruction, especially in, for example, hepatitis. Levels are also raised after myocardial infarction and in muscle disease.

The enzyme alanine aminotransferase is also found in high concentrations in the liver and to a lesser degree in the heart, kidney and in skeletal muscle. It catalyzes the following reaction:

$$\text{alanine} + \text{2-oxoglutarate} \rightleftharpoons \text{pyruvate} + \text{glutamate}$$

Increases in the serum level of this enzyme are usually found in liver conditions, especially hepatitis.

The indirect quantification of enzymes, in particular, the transaminases, aspartate aminotransferase and alanine aminotransferase in sample body fluids may involve contrasting a sample "blank" against a sample in which the enzymatic conversion of an analyte associated with the enzyme of interest has taken place.

To achieve enzymatic conversion of the analyte, the substrate specific enzyme (the transaminase), is allowed to act upon enzyme substrates known for use in quantification of the enzyme of interest. The change in the reaction composition with respect to the blank can be calculated by various methods which measure the change in absorbance of the composition. The change in absorbance correlates directly to the amount of transaminase present in the sample.

Whilst traditional methods such as colorimetric determination have proved adequate, enzymatic analysis has been shown to be vastly more accurate, reliable and simpler than these other methods when it comes to the determination of transaminase levels.

A commonly used method of quantification of transaminases in a sample is in a kinetic manner using a coupled enzyme reaction.

In the case of aspartate aminotransferase (AST), the oxaloacetate formed by the AST is converted to malate by including malate dehydrogenase (MDH) in the assay system. This is accompanied by the oxidation of the coenzyme nicotinamide adenine dinucleotide (NADH to NAD$^+$) which can be followed spectrophotometrically at 340 nm. Thus the reaction sequence is commonly as follows:

$$\text{L-aspartate} + \text{2-oxoglutarate} \xrightleftharpoons{\text{AST}} \text{oxaloacetate} + \text{L-glutamate}$$

$$\text{oxaloacetate} + \text{NADH} \xrightleftharpoons{\text{MDH}} \text{L-malate} + \text{NAD}^+$$

$$\text{sample pyruvate} + \text{NADH} \xrightleftharpoons{\text{LDH}} \text{lactate} + \text{NAD}^+$$

The third reaction is required to eliminate the potential presence of high levels of pyruvate in patient samples. The theory behind including high levels of the enzyme lactate dehydrogenase (LDH) is that if high levels are included in the reagent, in the event that a patient sample has a high level of pyruvate, the presence of NADH and LDH will quickly eliminate the sample pyruvate by converting it to lactate which will not interfere in the reaction. The need to load the reagent with LDH to eliminate this side reaction can affect the stability of the reagent by introducing more contaminants.

For alanine aminotransferase (ALT), the pyruvate formed by the ALT is converted to lactate by including lactate dehydrogenase in the reaction mixture. This is accompanied by the oxidation of the coenzyme NADH to NAD$^+$ which again can be followed spectrophotometrically at 340 nm. Thus the reaction sequence being carried out in using the reagent is as follows:

$$\text{L-alanine} + \text{2-oxoglutarate} \xrightleftharpoons{\text{ALT}} \text{pyruvate} + \text{glutamate}$$

$$\text{pyruvate} + \text{NADH} \xrightleftharpoons{\text{LDH}} \text{lactate} + \text{NAD}^+$$

$$\text{sample pyruvate} + \text{NADH} \xrightleftharpoons{\text{LDH}} \text{lactate} + \text{NAD}^+$$

The theory and methodology of the ALT measurement is similar to the AST reagent with the exception that with ALT only one endogenous enzyme, namely LDH is required for the measurement (as opposed to the requirement for LDH and MDH with AST). As such, fewer contaminants are introduced into the ALT reagents which generally means that their reconstituted shelf life can be a little longer than AST reagents.

For both reagents the rate of NAD$^+$ formation correlates to the concentration of transaminase originally present in the sample.

Urea is the major nitrogen-containing metabolic product of protein catabolism, being synthesized in the liver by hepatic enzymes of the liver and excreted predominantly through the kidneys. Elevated levels of urea in serum may be a consequence of impaired kidney function, liver disease, dietary changes, congestive heart failure, diabetes and infections.

The level of urea in human serum and urine may be detected by direct and indirect methods. Direct methods usually involve variations of the Fearon reaction. In this reaction system, diacetyl reacts with urea to form the chromogen diazine, which may be measured spectrophotometrically by its strong absorbance at 540 nm. The most common method of measurement of urea in human serum and urine involves an indirect coupled enzymatic reaction system. Urease, the first enzyme in the reaction system, is used to convert urea into ammonium and bicarbonate ions. Glutamate dehydrogenase (GLDH), the second enzyme in the reaction system, couples NADH and the ammonium ion to produce NAD$^+$ and glutamate. This reaction is followed spectrophotometrically at 340 nm, as NADH is converted to NAD$^+$. Alternatively, the ammonium ion may be quantitated by potentiometry or conductimetry.

Thus, the reaction process commonly used to determine urea concentration is as follows:

$$\text{Urea} + H_2O \xrightarrow{\text{Urease}} 2NH_3 + CO_2$$

$$NH_3 + \alpha\text{-ketoglutarate} + NADH \xrightarrow{\text{GLDH}} \text{L-glutamate} + NAD^+$$

The decrease in absorbance at 340 nm as NADH is converted to $NAD^+$ is measured and this is proportional to the concentration of urea in the original sample.

The major source of circulating ammonia is the gastrointestinal tract. Ammonia is metabolized in the liver, being converted to urea in the Krebs-Henseleit cycle. Elevated levels of ammonia in human serum is most often associated with advanced liver disease. Hyperammonemia has a toxic effect on the central nervous system.

The level of ammonia in human serum is most commonly measured by a direct, one stage enzymatic method, incorporating glutamate dehydrogenase. In this reaction, the conversion of ammonia, α-ketoglutarate and NADH (or NADPH) to glutamate and $NAD^+$ (or $NADP^+$) is measured spectrophotometrically at 340 nm.

The commonly used reaction sequence for determining the ammonia concentration of a sample is as follows:

$$NH_3 + \alpha\text{-ketoglutarate} + NADPH \xrightarrow{\text{GLDH}} \text{L-glutamate} + NADP^+$$

The decrease in absorbance at 340 nm as NADPH is converted to $NADP^+$ is measured and this is proportional to the concentration of ammonia in the patient sample.

Historically, as mentioned above, transaminase reagents have suffered from poor reconstituted stability. The stability of these reagents, especially in a single vial format is limited usually to approximately a maximum of one month under refrigerated conditions. The cause of this instability could be attributed both to the deterioration of endogenous ingredients in the reagents as well as instability of NADH in solution. The main causes of instability of the NADH in solution are related directly to the presence of endogenous reagent enzymes, namely LDH and MDH in the AST reagent and LDH in the ALT reagent. Commercial preparations of the endogenous enzymes MDH and LDH, whether they be of animal origin or microbial origin, contain contaminants which ultimately affect the reconstituted stability of NADH and consequently the stability of the reagents. These contaminants are usually low levels of AST and ALT, the enzymes it is desired to measure and NADH oxidase, all of which initiate the oxidation of NADH in the reagent.

The reagent pH can also have an effect on the instability of the NADH since NADH will rapidly decompose in solution, especially in an acidic medium. Most reagents for transaminase determination are formulated with a pH range of 7.3 to 8.0. The more alkaline the reagent, the greater the stability of NADH in solution.

Furthermore, ammonia and urea reagents also suffer from stability problems and the stability of these reagents in a single vial format and at refrigerated temperatures, has usually been limited to a maximum of one month in the case of ammonia and two months in the case of urea. The cause of this instability could be attributed to the deterioration of the endogeneous ingredients in the reagents, the instability of NADH or NADPH in solution and contamination by ammonia present in water used to reconstitute the reagent powder.

The main causes of instability of the NADH or NADPH in solution are related directly to the presence of endogenous reagent enzymes. The reagent pH can also have an effect on the instability of the NADH or NADPH as NADH and NADPH will rapidly decompose in solution, especially in an acidic medium.

NADPH is commonly employed in ammonia reagents (in preference to NADH), in order to overcome assay interference by endogeneous lactate dehydrogenase in patient sera. Endogeneous lactate dehydrogenase and pyruvate from the patient sample will specifically react with NADH in the following reaction sequence:

$$\text{sample pyruvate} + NADH \underset{\phantom{LDH}}{\overset{LDH}{\rightleftharpoons}} \text{lactate} + NAD^+$$

The maintenance of NADPH in solution will also be affected by the presence of contaminants of commercial preparations of glutamate dehydrogenase, which will initiate oxidation of NADPH in the ammonia reagent. Likewise, the presence of contaminants of commercial preparations of urease and glutamate dehydrogenase will initiate oxidation of NADH in the urea reagent.

One means of overcoming this difficulty relating to the stability of NADH and NADPH in solution has been to generate reduced coenzyme in the reagent just prior to its use.

One such method is described in Australian patent application AU-A-61906/90 to F. Hoffmann La Roche AG with particular regard to similar enzymatic systems for the measurement of serum bicarbonate and ammonia. In this disclosure the reduced coenzyme is generated in situ either simultaneously with or prior to reoxidation of the coenzyme by the analyte, substrate and specific enzymes. This is achieved by including in the reaction mixture an enzyme and enzyme substrate enabling the reduction of the oxidized coenzyme. The specific reaction disclosed and favoured by F. Hoffmann La Roche AG is:

$$NAD^+ + \text{Glucose-6-Phosphate(G-6-P)} \xrightarrow[\text{Dehydrogenase (G-6-P-DH)}]{\text{Glucose-6-Phosphate}}$$

$$H^+ + NADH + \text{6-phosphogluconolactone}$$

This makes available reduced nicotinamide adenosine dinucleotide.

The problem associated with this mode of generation of NADH is that a stable single vial reagent configuration is not possible.

To a certain extent F. Hoffmann La Roche AG have overcome this problem by dividing the reagent system into 2 vials. The first reagent comprises in the case of ammonia quantification, $NADP^+$ and G-6-P, and the second reagent α-ketoglutarate, G6PDH and GLDH. The determination reaction thus proceeds as follows:

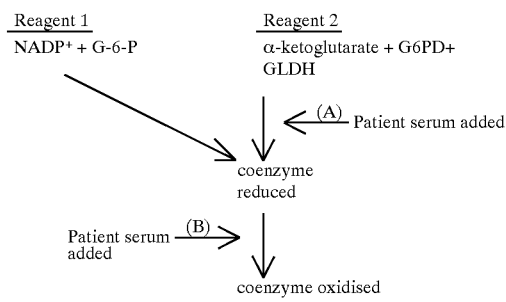

where (A) and (B) represent alternative, equivalent routes.

Difficulties remain, however, with this reagent system. Apart from the fact that two reagent vials are required thus increasing cost, inventory and waste, very accurate levels of glucose-6-phosphate are required and moreover, the system is limited to use in specific chemical analysers. As soon as the reagents are combined, generation of NADH from $NAD^+$ occurs by exhaustion of glucose-6-phosphate. Because glucose-6-phosphate is thus exhausted, stability of the combined reagent could be severely affected if the two reagents were to be combined and not immediately used. If inaccurate or excess levels of glucose-6-phosphate are present, the timing associated with incubation of the reagent becomes critical. Results may be falsely low absorbance changes and grossly inaccurate results.

One earlier solution also relating to the measurement of analyte levels described in U.S. Pat. No. 4,394,449 to Modrovich uses substrate/enzyme pairs to generate the reduced coenzyme as does the Roche solution, however, in this case glucose-6-phosphate is generated from glucose in accordance with the following:

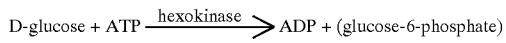

$NAD^+$ then reacts with the formed glucose-6-phosphate in the presence of the enzyme glucose-6-phosphate dehydrogenase to form NADH. Modrovich also includes both NADH and $NAD^+$ in the formulation such that when NADH is oxidized or destroyed, the $NAD^+$ present in the reagent will aid the regeneration of NADH. This is also a two vial reagent.

An early alternative is provided by Klose et al in U.S. Pat. No. 4,019,961. This invention relies on various separate reaction steps and an NADH regenerating enzymatic system. This system has the disadvantage of reliance on carrying out various reaction steps and separation steps making it a time consuming test. Furthermore, this reagent system is only suitable for substrates which can be phosphorylated.

The general problem associated with the NADH and NADPH generation mechanism adopted by each of the inventions described hereinabove, that is

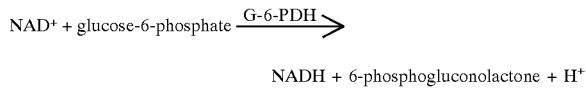

is that a single step reaction using a single vial is not possible because as soon as the patient serum is added to the reagent, two simultaneous reactions occur:
(a) a decrease in absorbance due to NADH (or NADPH) being converted to $NAD^+$ ($NADP^+$),
(b) generation of NADH (NADPH) from $NAD^+$ ($NADP^+$) resulting in an increase in absorbance.

These two reactions occur at similar velocities with the net result being a falsely low absorbance change and grossly inaccurate results.

Accordingly, it is an object of this invention to provide a reagent system for use in determination of serum analyte levels which substantially ameliorates the problems of prior art reagent systems used in enzymatic analysis of serum analyte levels relying on the oxidation of a coenzyme, particularly those problems which relate to endogenous or exogenous contamination of the reagent. It is a further object of this invention to provide an improved method of determination of the concentration of analyte levels in a patient sample, the method overcoming the problems associated with prior art methods including premature oxidation of the coenzyme determinant and the necessity for a multi-vial system to minimize degradation of the reagent.

To this end there is provided a reagent for enzymatic determination of an analyte concentration in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent.

There is also provided a reagent for enzymatic determination of the transaminase concentration in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent.

There is also provided a reagent for enzymatic determination of aspartate transaminase concentration in a patient wherein the degree of oxidation of a coenzyme is measured, characterised in that said reagent is stabilised against oxidation by a coenzyme reduction system comprising an enzyme and substrate pair selected so as to enable continuous regeneration of said coenzyme throughout storage of said reagent.

There is also provided a reagent for enzymatic determination of alanine aminotransferase concentration in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent.

There is provided a reagent for enzymatic determination of urea concentration in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent.

There is also provided a reagent for enzymatic determination of ammonia concentration in a patient wherein the degree of oxidation of a coenzyme is measured, characterized in that said reagent is stabilized against oxidation by a coenzyme reduction system comprising an enzyme and substrate pair selected so as to enable continuous regeneration of said coenzyme throughout storage of said reagent.

Preferably, the coenzyme reduction system comprises an enzyme and a substrate, said enzyme having incomplete specificity for said substrate, thereby resulting in a reduced rate of cross reactivity.

The reagent is preferably in a single vial configuration.

Throughout this specification the term "incomplete specificity" is used with respect to enzyme and substrate pairs wherein the substrate selected is not the natural substrate of the enzyme selected and thus has less than 100% cross specificity for the enzyme concerned.

This invention is predicated on the discovery that by coupling an enzyme and substrate having incomplete specificity for each other, the rate of coenzyme reduction is considerably slowed. By slowing down the reduction reaction, the essential components of the reagent can be contained within one storage vial, the contents being stabilized against contamination by the low level continuous regeneration of the coenzyme. By slowing down the process, the regeneration of NADH or NADPH can occur without affecting the measurement of the analytes. The regeneration can occur in the reagent when not in use and the velocity at which regeneration occurs can be fine tuned by adjusting the nature of the enzyme/substrate pair selected and the levels thereof.

In an alternate embodiment of the invention, there is provided a reagent for use in an enzymatic determination of an analyte concentration in a patient wherein the degree of oxidation of a coenzyme is measured, characterized in that said reagent is stabilized against oxidation by a coenzyme reduction system comprising an enzyme and substrate pair selected so as to enable regeneration of said coenzyme at a rate of 0.01–0.9 mAbs/min at 340 nm.

Preferably the rate of regeneration in a reagent according to this aspect of the invention is 0.05–0.4 mAbs/min, and most preferably the rate of regeneration is 0.05–0.25 mAbs/min at room temperature (18°–25° C.) and at 340 nm.

In a preferred embodiment of the invention, the degree of specificity between the substrate and enzyme of the coenzyme reduction system is preferably less than 100%, more preferably less than 50% and most conveniently less than 10% on an equimolar basis. Optimally, an enzyme/substrate pair having a cross-reactivity of less than 5% on an equimolar basis may be used.

The coenzymes preferably used in the reagent according to the invention are reduced nicotinamide adenine dinucleotide (NADH) and reduced nicotinamide adenine dinucleotide phosphate (NADPH), although coenzyme analogs such as nicotinamide hypoxanthine dinucleotide phosphate or thio-NADH may also be suitable.

Surprisingly, it has been found that reagents of the invention provide a further advantage, particularly for ammonia and urea reagents. NADH and/or NADPH levels will be depleted in the urea and ammonia reagents by the presence of contaminant ammonia, introduced with the water used to reconstitute the powder reagents. Likewise, ammonia in the air which dissolves into the liquid urea/ammonia reagents over time will deplete the levels of NADH and/or NADPH. The presence of a contaminating ammonia in ammonia and urea reagents cannot only lead to inaccurate determinations of urea and ammonia but can mean that the reaction with α-ketoglutarate and NADH in the presence of GLDH will occur prior to samples being added. This leads to depleted levels of NADH or NADPH and thus can lead to errors in determining ammonia and urea concentrations in samples. However, the present invention allows for the removal of the contaminating ammonia and also the regeneration of NADH or NADPH to allow accurate determination of ammonia and urea concentrations in patient samples.

Enzymes preferably utilized in the coenzyme reduction system for determination of the transaminase content of a serum sample may be glucose-6-phosphate dehydrogenase (G-6-P-DH) or glucose dehydrogenase.

Enzymes preferably utilized in the coenzyme reduction system for determination of the urea or ammonia content of a serum sample may be glucose-6-phosphate dehydrogenase (G-6-P-DH) or glucose dehydrogenase.

Enzymes such as formate dehydrogenase, glycerol dehydrogenase, leucine dehydrogenase, L-Alanine dehydrogenase, 3α-Hydroxy-steroid Dehydrogenase, L-lactate Dehydrogenase (from Lactobacillus sp.) or Glycerol-3-phosphate dehydrogenase may also be suitable. The preferred enzyme used for transaminase/ammonia and urea level determination reagents is glucose-6-phosphate dehydrogenase. This may be obtained from any suitable source, such as *Leuconostoc mesenteroides, Bacillus stearothermophilus, Zymomonas mobilus* or yeast.

Such enzymes are preferably derived from microbial sources. The incorporation into the reagent of enzymes from microbial sources has been found to minimize the presence of endogenous contaminants such as NADH oxidase and proteases which previously severely affected the stability of the reagents. The microbial enzymes also have the added advantage of being more thermostable, thereby improving their long term stability in solution.

The more preferred source of glucose-6-phosphate dehydrogenase is from *Leuconostoc mesenteroides*. If glucose-6-phosphate from *Bacillus stearothermophilus* or *Zymomonas mobilus* is used, the rate of reaction is reduced. Similarly, if yeast is used as the source of glucose-6-phosphate dehydrogenase, the coenzyme NADPH must be used as an alternative to NADH since yeast glucose-6-phosphate dehydrogenase is only specific for NADP$^+$. The appropriate amount of glucose-6-phosphate dehydrogenase present in the reagents according to the invention will vary according to the desired regeneration rate. Particularly preferred for the AST reagent, however, is an amount of approximately 2000 U/L to allow for deterioration over time in solution. For ALT the particularly preferred concentration is 2000 U/L. A preferred concentration for the urea reagent is 2000 U/L, and a preferred concentration for the ammonia reagent is 3500 U/L.

Bearing in mind that the selection of substrate and enzyme must be such that in the coenzyme reduction system they have incomplete specificity for each other, suitable substrates for use in the reagent according to the invention include ribose-5-phosphate, glucose-1-phosphate, 6-phosphogluconic acid, 2-deoxyglucose-6-phosphate, 2-deoxy-2-fluoroglucose-6-phosphate, 2-deoxy-2-chloroglucose-6-phosphate, 2-deoxy-2, 2-difluoroglucose-6-phosphate, 2-O-methylglucose-6-phosphate, mannose-6-phosphate, glucosamine-6-phosphate, 3-deoxyglucose-6-phosphate, 3-deoxy-3-fluoro-glucose-6-phosphate, 3-O-methylglucose-6-phosphate, allose-6-phosphate, ahrose-6-phosphate, 4-deoxy-4-fluoroglucose-6-phosphate, galactose-6-phosphate, 5-thio-glucose-6-phosphate, phosphonate analogs, glucose-6-stallate, β-D-glucose, D-galactose, 2-deoxyglucose, arabinose, xylose, 1-sorbose, D-mannose, D-fructose, D-lactose, D-sorbital, D-mannitol, saccarose, inositol, maltose.

Using NADH as the preferred coenzyme in the reagent, the preferred enzyme/substrate combination is glucose-6-phosphate dehydrogenase (G-6-P-DH)/D-glucose. Preferred alternative substrates for D-glucose are those for which, relative to the specificity between glucose-6-phosphate (G-6-P) and G-6-P-DH, the rate of reaction between the enzyme G-6-P-DH and the selected substrate is less than 50%, more preferably less than 10% and most preferably less than 5%. Again, bearing in mind the rate of regeneration required, the level of D-glucose most appropriate to the reagents according to the invention, and therefore preferred are about 100 mmol/L although levels up to 1000 mmol/L may be used. Solubility of the D-glucose in the reagent becomes an issue at the higher concentration levels.

Where the preferred combination of D-glucose/glucose-6-Phosphate dehydrogenase is used, the potassium phosphate ions may be introduced into the composition in the form of Potassium Phosphate Dibasic. A varying level of phosphate ions may be suitable depending on the desired rate of regeneration. However, when the concentration of D-glucose is approximately 100 mmol/L (but can vary between 20 and 200 mmol/L) for example, and the corresponding level of glucose-6-phosphate dehydrogenase is approximately 2000 U/L (but can vary between 500 and 3500 U/L), the level of phosphate ions that may be suitable may range from 2.0 mmol/L through to 20 mmol/L. Increasing the concentration of phosphate ions will increase the regeneration rate. The preferred level of phosphate ion addition is about 10 mmol/L for AST and about 5 mmol for ALT. For the urea reagent the preferred phosphate ion concentration is about 5 mmol and is also about 5 mmol for the ammonia reagent.

When the preferred combination of D-glucose and glucose-6-phosphate dehydrogenase is utilized, or indeed in any system in which no free phosphate is generated, it is essential to incorporate free phosphate ions into the reagent.

In particular, the free phosphate ions are required to form a non-specified complex with D-glucose to initiate the regeneration in the presence of glucose-6-phosphate dehydrogenase.

One preferred alternative to the use of D-glucose/G-6-P-DH is the use of glucose dehydrogenase (GLD) according to the following reaction wherein D-glucose is the 100% reactive substrate:

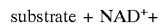

D-glucose + NAD⁺ $\xrightarrow{\text{GLD}}$ D-glucono-∂-lactone + NADH + H⁺

If glucose dehydrogenase is used as the enzyme, preferred substrates for reduction of the NAD coenzyme and their relative degree of cross reactivity when compared to D-glucose are:

| Substrate | Relative Activity |
| --- | --- |
| xylose | 8.9% |
| L-sorbose | 0.3% |
| D-mannose | 2.4% |
| D-fructose | 0.8% |
| D-galactose | 0.1% |
| D-lactose | 1.2% |
| D-sorbitol | 0.1% |
| inositol | 0.2% |
| maltose | 3.9% | wherein the figures represent the rate of reaction relative to that of glucose-dehydrogenase in the presence of the natural substrate 1β-D-glucose.

Alternatively, using glycerol dehydrogenase (GLY.DH) as the enzyme, suitable substrates in the reaction glycerol + NAD⁺ $\xrightarrow{\text{GLY.DH}}$ dihydroxyacetone + NADH + H⁺

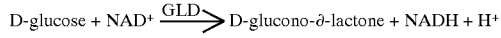

and their activity relative to glycerol (100%) are

| Substrate | Relative Activity |
| --- | --- |
| glycerol-α-monochlorohydrin | 48.5% |
| Ethylene glycol | 7.8% |
| 2,3-Butanediol | 52.6% | wherein leucine dehydrogenase (L.D) is used as the enzyme according to the reaction substrate + NAD⁺ +

$H_2O \underset{\longleftarrow}{\overset{L.D}{\longrightarrow}}$ α-ketoisocaproate + NH₃ + NADH + H⁺

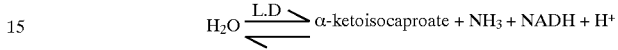

suitable substrates and their activity relative to L-leucine (100%) are

| Substrate | Relative Activity |
| --- | --- |
| L-valine | 74% |
| L-isoleucine | 58% |
| L-norvaline | 41% |
| L-norleucine | 10% |
| L-methionine | 0.6% |
| L-cysteine | 0.3% |

If L-alanine dehydrogenase (A.D) is used as the enzyme in a reaction system similar to that used for leucine dehydrogenase, a suitable substrate and its activity relative to L-alanine (100%) is

| Substrate | Relative Activity |
| --- | --- |
| L-serine | 5% |

3α-hydroxysteroid dehydrogenase (H.DH) may also be used as an enzyme in combination with the substrates listed below. Their activities relative to cholic acid are also listed.

| Substrate | Relative Activity |
| --- | --- |
| Lithocholic acid | 96% |
| Etiocholic acid | 60% |

Wherein, L-lactate dehydrogenase (LDH) from Lactobacillus sp. is used as the enzyme in the following reaction, pyruvate + NADH + H⁺ $\xrightarrow{\text{LDH}}$ L-lactate + NAD⁺

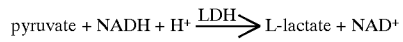

suitable substrates and their activity relative to L-lactate are:

| Substrate | Relative Activity |
| --- | --- |
| 2-oxoglutarate | 0.09% |
| oxoloacetate | 36% |

Wherein NADP⁺ is the coenzyme, for example from yeast, preferred substrate/enzyme combinations are:

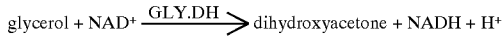

| | |
|---|---|
| G-6-P-DH/galactose-6-P | 25% |
| G-6-P-DH/2-deoxyglucose-6-P | 18% |
| G-6-P-DH/glucosamine-6-P | 2% |

The figures in on the right hand side represent the relative reactivity to that of a G-6-P-DH/G-6-P pair.

It is also possible using NADP$^+$ as coenzyme to combine as enzyme/substrate glycerol-3-phosphate dehydrogenase with dihydroxy acetone phosphate.

As described in the preamble to this specification, the other requirements of a reagent according to the invention for use in the determination of serum AST levels are lactate dehydrogenase, nicotinamide-adenine dinucleotide, reduced (NADH), malate dehydrogenase (MDH), aspartate and 2-oxoglutarate. In the case of ALT the malate dehydrogenase is not required and in the place of aspartate, L-alanine is required. In the case of the urea reagent, urease and α-ketoglutarate are also required, whilst α-ketoglutarate is also required in the ammonia reagent.

Aspartate is available as a variety of salts, such as sodium and potassium salts. The preferred salt according to the invention is potassium salt since it appears to be more soluble and is less hydrated than the sodium salt. A concentration range which may be acceptable in the reagents of the invention is 180–240 mmol/L. Most preferred is a final concentration of about 200 mmol/L, and it is noted that this is the IFCC recommended level.

The range of 2-oxoglutarate considered as being preferred for the reagents of the invention is about 1–15 mmol/L, however it is noted that high concentrations of this substrate could limit the amount of NADH that can be added to the composition since 2-oxoglutarate absorbs at 340 nm providing background absorbance to the NADH absorbance. By limiting the amount of 2-Oxoglutarate added to the composition the reagent can be utilized on most spectral analyzers without difficulty. A preferred concentration of this substrate for the AST and ALT reagents is about 12 mmol/L, which is again the level recommended by the IFCC. For the urea and ammonia reagents the preferred concentration is about 7.5 mmol/L.

The amount of alanine present in the ALT reagent is governed to a certain extent by the solubility of this component. In particular, a preferred range is 200–500 mmol/L although at the higher end of the range no appreciable increase in catalytic activity is observed. The most preferred concentration of this substrate is about 400 mmol/L for the reason of the solubility of this substance.

The level of coenzyme in the reagent will vary according to the following factors:

linearity required in measurement
wavelength chosen
sample to reagent volume ratio
photometric system of the analyser selected.

In general, increasing the sample volume improves the sensitivity but decreases the linearity of the reading obtained, whereas decreasing the sample volume improves linearity at the expense of losing sensitivity.

The preferred wavelength of measurement is 320–400 nm, however, the level of coenzyme used should be adjusted so that the absorbance preferably does not exceed 2.0 A. The preferred wavelength of absorbance according to the invention is 340 nm.

MDH is preferably obtained from microbial sources so as to limit the risk of endogenous contamination and because it exhibits superior characteristics with regard to thermal stability. Appropriate levels are in the range 150–1500 U/L, more preferably 200–800 U/L. The most preferred level according to the invention is about 250 U/L.

In the AST reagent, LDH participates in the removal of the endogenous sample pyruvate. The level of LDH preferably incorporated into the AST reagent of the invention was such that a 1.0 mmol/L sample of pyruvate was cleared within 1 minute utilising a sample to reagent ratio of 1:10. This level was determined to be approximately 2000 U/L.

In the ALT reagent, the LDH participates in two reactions, (i) the coupled enzyme reaction for measurement of ALT, and (ii) the removal of the endogenous sample pyruvate. The level of LDH incorporated, as with the AST reagent was such that the reagent would remove up to 1.0 mmol/L of sample pyruvate in 1 minute. The main reaction can then be measured after 1 minute without interference from the endogenous sample pyruvate. The minimum level of LDH required for endogenous pyruvate clearance was determined to be about 1500 U/L. The preferred amount incorporated into the ALT reagent of the invention was about 2000 U/L.

In the urea reagent, the minimum urease activity required at pH 8.5, as the non-rate limiting enzyme in the kinetic mode of assay is about 5000 U/L. Quantities in excess of this may be included to increase the long term stability of the reagent.

The preferred mode of analyte measurement in the urea and ammonia reagents is based on kinetic principles. As glutamate dehydrogenase (GLDH) is the rate limiting enzyme in the formulation, the level of GLDH activity included in the reagent is critical to the linearity of the assay. The level of GLDH activity required will also vary as a function of the pH of the reagent system. A suitable range of GLDH activity may vary between 250–10000 U/L. Most suitable enzymes are those from microbial origins, as commercial GLDH preparation from animal sources are usually less stable and likely to contain higher levels of NADH oxidase activity as a contaminant. The preferred GLDH activity for the urea reagent, at pH 8.50, is about 500 U/L and for the ammonia reagent, at pH 8.50, is about 8500 U/L.

The reagents according to the invention may include in addition to the coenzyme reduction system and other essential substrates and enzymes necessary to determine the analyte concentration, preservatives, chelating agents, surface active agents, protease inhibitors, buffers, cofactors, antibacterials and other constituents which perform stability enhancing functions but do not materially affect the characteristics of the invention.

The primary criteria for selecting a buffer is such that it will have good buffering capacity at the selected pH with minimal binding of divalent cations. The pH and buffer system for the AST and ALT reagents are selected according to the recommendations of the International Federation of Clinical Chemistry (IFCC) for the measurement of transaminases. A general rule of thumb is that a buffer may be considered effective if its pKa is ±1.0 pH units from the chosen pH. A preferred pH of the reagent according to the invention is 7–9. For aspartate transaminase, optimal catalytic activity occurs at approximately pH 7.0–8.2 at 30° C. The most preferred pH for the AST reagent is about 8.1±0.1 at 20° C. since at this pH NADH is stable. For the ALT reagent, maximal catalytic activity occurs at a pH range of about 7.3–7.9 at 20° C. The most preferred pH for the ALT reagent is about 7.7 at 20° C. At these preferred pHs a compromise is reached between optimal enzyme activity and the stability of the enzymes and coenzyme in solution. A lower pH may result in increased degradation of the coenzyme.

The preferred buffer system for the urea reagent is Tris at pH 8.50, although the range pH 7.5–9.5 may be considered acceptable. The preferred concentration of buffer for effective buffering capacity is 100 mM Tris, although the range 20–200 mM Tris may be used. A wide range of alternative buffers may be used in this reagent system, which provide effective buffering capacity within the pH 7.5–9.5 range.

The preferred buffer system for the ammonia reagent is Tris at pH 8.5–9.0, although anywhere in the range pH 7.5–9.5 may be considered acceptable. The preferred concentration of buffer for effective buffering capacity is 100 mM Tris, although anywhere in the range 20–200 mM Tris may be used.

Suitable buffers for the AST and ALT reagents include HEPES, 4-morpholine propanesulfonic acid (MOPS) or 2-[tris(hydroxymethyl)methylamino]-1-ethane-sulfonic acid (TES) or diethanolamine or the other GOOD buffers, Tricine, Bicine, TEA and TAPS, TAPSO and POPSO. The preferred buffer according to the invention is TRIS having a total concentration preferably of 30–150 mmol/L, and more preferably approximately 70–100 mmol/L, although about 80 mmol/L is preferred. At higher buffer concentrations AST is increasingly inhibited. It is noted that phosphate buffers appear to increase the rate of decomposition of the NADH and to inhibit association of pyridoxal-5-phosphate (P-5-P) with the transaminase apoenzyme. The sample to be tested may be diluted with any suitable diluent if desired, such as deionized water or saline. In addition to the above-mentioned buffers suitable for AST and ALT reagents, the following GOOD buffers are also suitable for the ammonia and urea reagents: CAPSO, CHES and AMPSO.

Preservatives such as sodium azide ($NaN_3$), hydroxybenzoic acid, gentamicin, Thymol and mercury-free preservatives available from Boehringer Mannheim such as methylisothiazolone are suitable. The appropriate level is such that the preservative retains its preservative properties for at least 6–8 months when stored at 2°–8° C. without inhibiting the enzymes present in the reagent. A suitable range fulfilling these criteria is 0.1–1.0 g/L.

A variety of chelating agents such as EDTA, EGTA, N-(2-hydroxyethyl)ethylenediaminetriacetic acid (HEDTA), etc. are also suitable as non-specific stabilisers. In the AST and ALT reagents of the invention EDTA has been preferably utilised at a level of about 2.0–10.0 mmol/L to stabilize the 2-oxoglutarate. This is available as a tetrasodium salt as well as a potassium salt, but the preferred salt according to the invention is the disodium salt. In the urea and ammonia reagents, the EDTA is present in the range of 0.2 to 10 mM. A particularly preferred concentration of EDTA is 1 mM.

Enzyme stabilizers may also be incorporated into the reagents of the invention. A preferred stabilizer is Bovine Serum Albumin, protease-free grade. Others suitable may include bovine gamma globulin, N-acetyl cysteine and glycerol.

Suitable defoaming agents may also be added if desired. Surfactants which may be used include Zwitterionic surfactants and non-ionic surfactants at levels which do not inhibit enzymes present in the reagents.

In another aspect of the invention there is provided an improvement in an enzymatic method of determination of an analyte concentration in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

There is also provided an improvement in an enzymatic method of determination of the transaminase concentration in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

There is also provided an improvement in an enzymatic method of determination of the aspartate aminotransferase in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

There is also provided an improvement in an enzymatic method of determination of the alanine aminotransferase in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

There is also provided an improvement in an enzymatic method of determination of the urea concentration in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

There is also provided an improvement in an enzymatic method of determination of the ammonia concentration in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent.

In a preferred method according to this aspect of the invention, the enzyme of the enzyme and substrate pair has incomplete specificity for said substrate thereby reducing the rate of cross reactivity between enzyme and substrate.

In a preferred embodiment of this aspect of the invention, the coenzyme reduction system comprises an enzyme and substrate having a specificity for each other, relative to the specificity of the enzyme for its natural substrate, of less than 100%, preferably less than 50% and most conveniently less than 10%. Most conveniently, the specificity of the enzyme/substrate pair for each other, relative to the specificity of the enzyme for its natural substrate, is less than 5%, desirably approximately 2%.

The selection of coenzyme, substrate and enzyme may be made from those mentioned hereinabove in relation to the reagents of the invention, depending on the analyte to be assessed.

In one embodiment of this aspect of the invention, the preferred components of the coenzyme reduction system used for determination of analyte concentration are NADH, G-6-P-DH and D-glucose such that the regeneration reaction taking place is

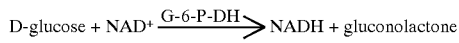

Due to the low specificity of G-6-P-DH for D-glucose this regeneration reaction is slow and thus not competitive with the main reactions involved in the determination of analyte levels.

PREFERRED EMBODIMENTS

In one preferred embodiment of the invention, the ALT reagent essentially comprises

| G-6-P-DH | } | coenzyme reduction |
| --- | --- | --- |
| D-glucose | } | system |
| L-alanine | | substrate |
| LDH | | substrate specific enzymes |
| NADH | | coenzyme |
| $K_2HPO_4$ | | activator |
| 2-oxoglutarate | | substrate |

In addition, there is preferably included TRIS buffer, TRIS HCl, EDTA-disodium, Bovine Serum Albumin and sodium azide.

One ALT reagent formulated in accordance with the invention is as follows:

TABLE 1

| RAW MATERIAL | MOLECULAR WEIGHT | QUANTITY/LITER |
| --- | --- | --- |
| TRIS Buffer | 121.14 | 1.5–3.5 g |
| TRIS-HCl | 157.60 | 8.0–14.0 g |
| L-Alanine | 89.09 | 34.0–45.0 g |
| α-ketoglutarate, Na salt (anhydrous) | 190.1 | 0.5–3.5 g |
| EDTA-Disodium | 372.24 | 1.0–3.0 g |
| Bovine Serum Albumin | | 0.1–2.0 g |
| NADH, $Na_2.3H_2O$ | 763.5 | 0.1–0.3 g |
| Potassium Phosphate dibasic ($K_2HPO_4$) | 174.18 | 0.3–1.3 g |
| Sodium Azide | 65.01 | 0.1–1.0 g |
| LDH microbial | | 2000–5000 U |
| G-6-PDH | | 200–3000 U |
| D-Glucose | 180.16 | 15.0–21.0 g |

In particular one preferred ALT reagent according to the invention is formulated as follows:

TABLE 2

| RAW MATERIAL | MOLECULAR WEIGHT | CONCEN-TRATION | QUANITY/LITER |
| --- | --- | --- | --- |
| TRIS Buffer | 121.14 | 18 mM | 2.18 g |
| TRIS-HCl | 157.60 | 70 mM | 11.03 g |
| L-Alanine | 89.09 | 440 mM | 39.2 g |
| α-ketoglutarate, Na salt (anhydrous) | 190.1 | 13.2 mM | 2.51 g |
| EDTA-Disodium | 372.24 | 5.5 mM | 2.04 g |
| Bovine Serum Albumin | | 0.1% | 1.00 g |
| NADH, $Na_2.3H_2O$ | 763.5 | 0.26 mM | 0.199 g |
| Potassium Phosphate dibasic ($K_2HPO_4$) | 174.18 | 5 mM | 0.87 g |
| Sodium Azide | 65.01 | 7.7 mM | 0.50 g |
| LDH microbial | | | 4000 U |
| G-6-PDH | | | 2000 U |
| D-Glucose | 180.16 | 100 mM | 18.016 g |

The formulation is 10% concentrated to allow for sample dilution.

In one preferred embodiment of the invention, the AST reagent essentially comprises

| G-6-P-DH | } | coenzyme reduction |
| --- | --- | --- |
| D-glucose | } | system |
| L-aspartate | | substrate |
| LDH | | substrate specific |
| MDH | | enzymes |
| NADH | | coenzyme |
| $K_2HPO_4$ | | activator |
| 2-oxoglutarate | | substrate |

In addition, there is preferably included TRIS buffer, TRIS HCl, EDTA-disodium, Bovine Serum Albumin and sodium azide.

One AST reagent formulated in accordance with the invention is as follows:

TABLE 3

| RAW MATERIAL | MOLECULAR WEIGHT | QUANTITY/LITER |
| --- | --- | --- |
| TRIS Buffer | 121.14 | 2.0–6.0 g |
| TRS-HCl | 157.60 | 6.0–11.0 g |
| L-Aspartate, K salt | 172.2 | 34.0–43.0 g |
| α-ketoglutarate, Na salt (anhydrous) | 190.1 | 0.5–4.5 g |
| EDTA-Disodium | 372.24 | 1.0–3.0 g |
| Bovine Serum Albumin | | 0.1–2.0 g |
| NADH, $Na_2.3H_2O$ | 763.5 | 0.1–0.3 g |
| Potassium Phosphate dibasic ($K_2HPO_4$) | 174.18 | 0.3–2.0 g |
| Sodium Azide | 65.01 | 0.1–1.0 g |
| LDH microbial | | 1000–4000 U |
| G-6-PDH (Toyobo) Leuconostoc mesenteroides | | 1000–4500 U |
| D-Glucose | 180.16 | 15.0–21.0 g |
| MDH microbial | | 100–600 U |

In particular one preferred AST reagent according to the invention is formulated as follows:

TABLE 4

| RAW MATERIAL | MOLECULAR WEIGHT | CONCEN-TRATION | QUANITY/LITER |
| --- | --- | --- | --- |
| TRIS Buffer | 121.14 | 31.2 mM | 3.78 g |
| TRIS-HCl | 157.60 | 56.8 mM | 8.95 g |
| L-Aspartate, K salt | 172.2 | 220 mM | 37.88 g |
| α-ketoglutarate, Na salt (anhydrous) | 190.1 | 13.2 mM | 2.51 g |
| EDTA-Disodium | 372.24 | 5.5 mM | 2.04 g |
| Bovine Serum Albumin | | 0.1% | 100 g |
| NADH, $Na_2.3H_2O$ | 763.5 | 0.26 mM | 0.199 g |
| Potassium Phosphate dibasic ($K_2HPO_4$) | 174.18 | 10.0 mM | 1.74 g |
| Sodium Azide | 65.01 | 7.7 mM | 0.50 g |
| LDH microbial | | | 2000 U |
| G-6-PDH Leuconostoc mesenteroides | | | 2000 U |
| D-Glucose | 180.16 | 100 mM | 18.016 g |
| MDH microbial | | | 200 U |

The formulation is 10% concentrated to allow for sample dilution.

In a preferred embodiment of the invention the urea reagent essentially comprises:

| G-6-P-DH | } | coenzyme reduction |
| --- | --- | --- |
| D-glucose | } | system |
| Urease | | analyte specific enzyme |
| α-ketoglutarate | | substrate |
| NADPH | | coenzyme |
| $K_2HPO_4$ | | activator |
| GLDH | | substrate specific enzyme |

One urea reagent formulated in accordance with the invention is as follows:

TABLE 5A

| RAW MATERIAL | MOLECULAR WEIGHT | QUANTITY/liter |
|---|---|---|
| TRIS Buffer | 121.14 | 5.0–10.0 g |
| TRS-HCl | 157.60 | 3.5–9.5 g |
| α-ketoglutarate, Na salt (anhydrous) | 190.1 | 0.5–3.5 g |
| EDTA-Disodium | 372.24 | 0.1–1.0 g |
| NADH, $Na_2.3H_2O$ | 763.5 | 0.1–0.3 g |
| Potassium Phosphate dibasic ($K_2HPO_4$) | 174.18 | 0.3–2.0 g |
| Bovine Serum Albumin | | 0.05–2.0 g |
| Sodium Azide | 65.01 | 0.1–1.0 g |
| D-Glucose | 180.16 | 3.0–21.0 g |
| Urease (microbial) | | 4000–9000 U |
| GLDH (microbial) | | 250–1000 U |
| G-6-PDH Leuconostoc mesenteroides | | 1000–4500 U |

In particular, a preferred urea reagent according to the invention is formulated as follows:

TABLE 5B

| RAW MATERIAL | MOLECULAR WEIGHT | CONCEN-TRATION | QUANTITY/Liter |
|---|---|---|---|
| TRIS | 121.14 | 61.3 mM | 7.43 g |
| TRIS-HCl | 157.60 | 38.7 mM | 6.10 g |
| α-ketoglutarate, Na salt (anhydrous) | 190.1 | 7.5 mM | 1.43 g |
| EDTA-Disodium | 372.24 | 1.0 mM | 0.372 g |
| NADH, $Na_2.3H_2O$ | 763.5 | 0.28 mM | 0.214 g |
| Potassium Phosphate dibasic ($K_2HPO_4$) | 174.18 | 5.0 mM | 0.871 g |
| Bovine Serum Albumin | | 0.05% | 0.50 g |
| Sodium Azide | 65.01 | 7.7 mM | 0.50 g |
| D-Glucose | 180.16 | 100 mM | 18.016 g |
| Urease (microbial) | | | 6500 U |
| GLDH (microbial) | | | 500 U |
| G-6-PDH Leuconostoc Mesenteroides | | | 2000 U |

In one preferred embodiment of the invention the ammonia reagent essentially comprises:

| | |
|---|---|
| G-6-P-DH | coenzyme reduction system |
| D-glucose | |
| α-ketoglutarate | substrate |
| NADPH | coenzyme |
| $K_2HPO_4$ | activator |
| GLDH | substrate specific enzyme |

In addition there is preferably included TRIS buffer, TRIS HCl, EDTA-disodium, ADP-K, bovine serum albumin and sodium azide.

One ammonia reagent formulated in accordance with the invention is as follows:

TABLE 6A

| RAW MATERIAL | MOLECULAR WEIGHT | QUANTITY/liter |
|---|---|---|
| TRIS | 121.14 | 5.0–10.0 g |
| TRIS-HCl | 157.60 | 3.5–9.5 g |
| α-ketoglutarate, Na salt (anhydrous) | 190.1 | 0.5–3.5 g |
| EDTA-Disodium | 372.24 | 0.1–1.0 g |
| NADPH, $Na_4.4H_2O$ | 905.4 | 0.1–0.35 g |
| ADP-K | 501.3 | 0–1.0 g |
| Potassium Phosphate dibasic ($K_2HPO_4$) | 174.18 | 0.3–2.0 g |
| Bovine Serum Albumin | | 0.05–2.0 g |
| Sodium Azide | 65.01 | 0.1–1.0 g |
| D-Glucose | 180.16 | 3–21 g |
| GLDH (microbial) | | 6000–10000 U |
| G-6-PDH Leuconostoc Mesenteroides | | 1000–4000 U |

In particular, a preferred urea reagent according to the invention is formulated as follows:

TABLE 6B

| RAW MATERIAL | MOLECULAR WEIGHT | CONCEN-TRATION | QUANTITY/liter |
|---|---|---|---|
| TRIS | 121.14 | 61.3 mM | 7.43 g |
| TRIS-HCl | 157.60 | 38.7 mM | 6.10 g |
| α-ketoglutarate, Na salt (anhydrous) | 190.1 | 7.5 mM | 1.43 g |
| EDTA-Disodium | 372.24 | 1.0 mM | 0.372 g |
| NADPH, $Na_4.4H_2O$ | 905.4 | 0.28 mM | 0.254 g |
| ADP-K | 501.3 | 2 mM | 1.0 g |
| Potassium Phosphate dibasic ($K_2HPO_4$) | 174.18 | 5.0 mM | 0.871 g |
| Bovine Serum Albumin | | 0.05% | 0.50 g |
| Sodium Azide | 65.01 | 7.7 mM | 0.50 g |
| D-Glucose | 180.16 | 100 mM | 18.016 g |
| GLDH (microbial) | | | 8500 U |
| G-6-PDH Leuconostoc Mesenteroides | | | 3500 U |

Although it is preferred that the reagents of the invention be formulated in a single vial configuration, it also possible that they be formulated in a two vial configuration. The regeneration component of the formulation need only be incorporated in one of the vials. In particular, the IFCC recommends that for ALT and AST reagents, the 2-oxoglutarate is formulated as a separate component to the remainder of the formulation. Reagent A (excluding the 2-oxoglutarate) may be incubated with the patient sample for a period of 5–10 minutes during which time, all side reactions are allowed to go to completion. After the incubation period, the 2-oxoglutarate can be added to commence the main reaction. As an alternative to using the 2-oxoglutarate as the starter component, it may also be possible to use the aspartate or alanine in the same way since the presence of the 2-oxoglutarate protects the AST or ALT from inactivation during the side reactions. The regeneration system comprising the unmatched pair of enzyme and substrate should be added to the component of the two vial system which includes NADH.

If a two vial system is used, it is recommended that the formulation include P-5-P since during the incubation period, in the presence of the sample, the addition of the P-5-P to the serum activates the apo-enzymes and permits the measurements of total AST and ALT catalytic activity concentrations in the serum provided that saturation with P-5-P is complete. The preferred level of P-5-P for use in a two vial system is about 80–120 μmol/L, with a more preferred level being 100 μmol/L.

EXAMPLE 1

The stability of four particular reagents formulated in accordance with the invention was tested as follows:

FORMULATION

AST reagent

TABLE 7A

| TRIS Buffer | 3.78 g/L |
|---|---|
| TRIS HCl | 8.95 g/L |
| Aspartate | 37.88 g/L |
| α-ketoglutarate, Na salt (anhydrous) | 2.51 g/L |
| Sodium Azide | 0.50 g/L |
| Bovine Serum Albumin | 1.0 g/L |
| NADH.$Na_2$.$3H_2O$ | 0.199 g/L |
| EDTA-Disodium | 2.04 g/L |
| Potassium Phosphate dibasic ($K_2HPO_4$) | 0.87 g/L |
| D-Glucose | 18.016 g/L |
| G-6-PDH(L.Mesenteroides) | 3500 U/L |
| D-LDH (microbial) | 2000 U/L |
| MDH (microbial) | 650 U/L |

TABLE 7B

| TRIS Buffer | 4.35 g/L |
|---|---|
| TRIS HCl | 8.31 g/L |
| L-Aspartate, K salt | 37.88 g/L |
| α-ketoglutarate, Na salt (anhydrous) | 2.51 g/L |
| Sodium Azide | 0.50 g/L |
| Bovine Serum Albumin | 0.50 g/L |
| NADH, $Na_2$.$3H_2O$ | 0.234 g/L |
| EDTA-Disodium | 1.86 g/L |
| Potassium Phosphate dibasic ($K_2HPO_4$) | 1.74 g/L |
| D-Glucose | 18.016 g/L |
| G-6-PDH (Toyobo) Luconostoc mesenteroids | 2000 U/L |
| LDH | 2000 U/L |
| MDH (microbial) | 200 U/L |

ALT Reagent

TABLE 8A

| TRIS Buffer | 2.18 g/L |
|---|---|
| TRIS HCl | 11.0 g/L |
| L-Alanine | 39.2 g/L |
| α-ketoglutarate, Na salt (anhydrous) | 2.51 g/L |
| Sodium Azide | 0.50 g/L |
| Bovine Serum Albumin | 1.0 g/L |
| NADH, $Na_2$$3H_2O$ | 0.199 g/L |
| EDTA-Disodium | 2.04 g/L |
| Potassium Phosphate dibasic ($K_2HPO_4$) | 0.87 g/L |
| D-Glucose | 18.016 g/L |
| G-6-PDH (Luconostoc Mesenteroides) | 3500 U/L |
| LDH (microbial) | 3000 U/L |

TABLE 8B

| TRIS Buffer | 3.27 g/L |
|---|---|
| TRIS HCl | 11.03 g/L |
| L-Alanine | 39.2 g/L |
| α-ketoglutarate, Na salt (anhydrous) | 2.51 g/L |
| Sodium Azide | 0.50 g/L |
| Bovine Serum Albumin | 0.50 g/L |
| NADH, $Na_2$$3H_2O$ | 0.234 g/L |
| EDTA Disodium | 1.86 g/L |
| Potassium Phosphate dibasic ($K_2HPO_4$) | 0.87 g/L |
| D-Glucose | 18.016 g/L |
| G-6-PDH (Luconostoc Mesenteroides) | 2000 U/L |
| LDH (microbial) | 4000 U/L |

STORAGE CONDITIONS capped and refrigerated (2°–8° C.)

SPECTROPHOTOMETRIC PARAMETERS (Shimadzu PC2101)

| reaction temperature | 37° C. |
|---|---|
| sample to reagent volume | 1:10 to 1:25 |
| wavelength | 340 nm |
| cuvette path length | 1 cm |

The lag phase of the measurement is approximately 1 minute or less and the time for measurement is up to 3 minutes post lag-phase.

These spectrophotometric parameters were used to determine the following

Initial absorbance of reagent at 340 nm regeneration rate at 20° C. (expressed in mAbs/min)

The Cobas Mira was used to determine recoveries on control standards.

The following results were obtained:

TABLE 9A

ARSORBANCE DATA FOR AST AND ALT REAGENTS SHOWN IN TABLES 7A and 8A

| Storage at 8° C. (weeks) | Absorbance at 340 nm | |
|---|---|---|
| ↓ | AST REAGENT | ALT REAGENT |
| FRESH REAGENT | 1.88 | 1.99 |
| 1 | 1.77 | 1.95 |
| 3 | 1.72 | 1.88 |
| 6 | 1.65 | 1.78 |
| 10 | 1.54 | 1.64 |
| 15 | 1.40 | 1.46 |
| 20 | 1.25 | 1.29 |
| 25 | 1.18 | 1.18 |
| 29 | 1.13 | 1.10 |
| 33 | 1.07 | 1.01 |

TABLE 9B

ABSORBANCE DATA FOR AST AND ALT REAGENTS SHOWN IN TABLES 7B AND 8B

| Storage at 2–6° C. (days) | Absorbance at 340 nm | |
|---|---|---|
| ↓ | AST REAGENT | ALT REAGENT |
| FRESH REAGENT | 1.83 | 1.86 |
| 22 | 1.82 | 1.81 |
| 29 | 1.8 | 1.8 |
| 60 | 1.73 | 1.7 |
| 92 | 1.67 | 1.61 |
| 125 | 1.6 | 1.52 |
| 159 | 1.52 | 1.41 |
| 187 | 1.46 | 1.33 |
| 194 | 1.45 | 1.32 |

The following Tables (Table 10A and 10B), provide evidence for the continued functionality of both AST and ALT reagents over 7 months. For each run, a high and low pool of AST and ALT serum was run using both freshly prepared reagent and reagent stored at 8° C. at different time intervals.

TABLE 10A

CONTROL SERA RECOVERIES FOR AST AND ALT REAGENTS SHOWN IN TABLES 7A AND 8A

| | ALT REAGENT (U/L) | | | | AST REAGENT (U/L) | | | |
| --- | --- | --- | --- | --- | --- | --- | --- | --- |
| | Fresh reagent | | Reagent stored at 8° C. | | Fresh reagent | | Reagent stored at 8° C. | |
| Storage at 8° C. (weeks) / serum pool → | low | high | low | high | low | high | low | high |
| 0  | 40 | 156 | 42 | 152 | 45 | 188 | 45 | 192 |
| 4  | 38 | 154 | 42 | 162 | 45 | 185 | 46 | 191 |
| 9  | 41 | 150 | 38 | 151 | 46 | 182 | 46 | 194 |
| 12 | 39 | 157 | 42 | 152 | 46 | 189 | 46 | 187 |
| 15 | 32 | 133 | 33 | 132 | 40 | 163 | 38 | 164 |
| 25 | 32 | 121 | 33 | 117 | 38 | 180 | 39 | 180 |
| 29 | 31 | 117 | 32 | 112 | 33 | 164 | 37 | 170 |

TABLE 10B

CONTROL SERA RECOVERIES FOR AST AND ALT REAGENTS SHOWN IN TABLES 7B AND 8B

| Storage (days) | Reagent stored at 8° C. | | Reagent stored at 4° C. | | Reagent stored at 20° C. | | Reagent stored at 4° C. | |
| --- | --- | --- | --- | --- | --- | --- | --- | --- |
| serum pool → | low | high | low | high | low | high | low | high |
| 0   | 32 | 123 | 32 | 123 | 40 | 186 | 40 | 186 |
| 7   | 33 | 120 | —  | —   | 41 | 191 | —  | —   |
| 14  | 32 | 121 | —  | —   | 41 | 184 | —  | —   |
| 21  | 33 | 121 | 33 | 122 | 41 | 182 | 40 | 184 |
| 28  | 32 | 120 | 32 | 120 | 41 | 185 | 40 | 184 |
| 35  | 33 | 118 | 33 | 117 | 42 | 185 | 44 | 183 |
| 60  | —  | —   | 33 | 120 | —  | —   | 41 | 185 |
| 92  | —  | —   | 36 | 122 | —  | —   | 45 | 190 |
| 125 | —  | —   | 35 | 123 | —  | —   | 44 | 189 |
| 159 | —  | —   | 36 | 123 | —  | —   | 43 | 188 |
| 187 | —  | —   | 35 | 125 | —  | —   | 44 | 187 |

TABLE 11A

LINEARITY STUDIES FOR AST AND ALT REAGENTS SHOWN IN TABLES 7A AND 8A

| AST REAGENT (U/L) | | | ALT REAGENT (U/L) | | |
| --- | --- | --- | --- | --- | --- |
| EXPECTED | OBSERVED | | EXPECTED | OBSERVED | |
| ↓ | MASTER BATCH | TRIAL REAGENT | ↓ | MASTER BATCH | TRIAL REAGENT |
| 400 | 393 | 389 | 380 | 380 | 357 |
| 200 | 182 | 182 | 120 | 121 | 119 |
| 100 | 98  | 96  | 60  | 65  | 63  |
| 50  | 50  | 51  | 30  | 34  | 28  |

TABLE 11B

LINEARITY STUDIES FOR AST AND ALT REAGENTS SHOWN IN TABLES 7B AND 8B

| AST REAGENT (U/L) | | | ALT REAGENT (U/L) | | |
| --- | --- | --- | --- | --- | --- |
| | OBSERVED | | | OBSERVED | |
| EXPECTED | FRESH REAGENT | 200 DAYS AT 4° C. | EXPECTED | FRESH REAGENT | 200 DAYS AT 4° C. |
| 120 | 122 | 113 | 141 | 137 | 133 |
| 240 | 241 | 237 | 282 | 285 | 273 |
| 300 | 301 | 295 | 353 | 353 | 352 |
| 360 | 360 | 357 | 424 | 422 | 416 |
| 420 | 420 | 416 | 494 | 493 | 476 |
| 480 | 479 | 472 | 565 | 560 | 551 |
| 540 | 538 | 527 | 635 | 635 | 621 |
| 600 | 598 | 596 | 706 | 710 | 684 |

Note: Trial reagent has been stored at 8° C. for a period of 31 weeks The Master batch was freshly reconstituted for this study.

From the results presented it is evident that the regeneration AST and ALT reagents are exhibiting at least 6–7 months stability when stored capped at 2°–8° C. The reagent must have an initial absorbance of 1.0 A to be functional. After 7 months the reagent still has an absorbance of at least 1.0 A.

From the results obtained in Table 10A and 10B it is clear that there are no significant differences in control sera recoveries obtained with fresh reagent as opposed to reagent stored at 8° for up to 29 weeks. Results presented in Tables 11A and 11B indicate that AST and ALT reagents incorporating coenzyme regeneration technology are still able to meet linearity specifications after 31 weeks storage at 8° C.

The incorporation of the regeneration system according to the invention has resulted in an increase in reconstituted stability of a serum AST and ALT measurement capped reagent from 1 month at 2°–8° C. to at least 6–8 months at 2°–8° C.

EXAMPLE 2

Urea reagents were prepared with ingredients as described in Table 5B above, except that 0.33 mM NADH was incorporated into the formulations, and the level of D-glucose was reduced to 20 mM for one of the reagents.

The formulations thus prepared were at pH 8.5. A conventional urea reagent formulation was used as a control. Reagents were prepared with a level of 0.15 mM ammonia introduced into the reagent system (final concentration) as a contaminant. This level of ammonia contaminant is sufficient to consume 0.15 mM NADPH in the respective reagents—equivalent to 0.93 absorbance units at 340 nm. After reaction completion (i.e. clearance of ammonia in the reagent formulation), the absorbance of the various solutions (placed in sealed cuvettes) was monitored over time on a Shimadzu spectrophotometer at 340 nm, and at a temperature of 20° C.

The results presented in FIG. 1 show the time dependent regeneration of NADH from $NAD^+$ in the urea reagent formulation of the invention after contamination with 0.15 mM ammonia.

In FIG. 1:

Panel A shows that NADH regeneration for a conventional urea reagent;

Panel B shows the NADH regeneration of a urea reagent containing 5 mM sodium phosphate, 2000 U/L G-6-PDH and 20 mM D-glucose;

Panel C shows the NADH regeneration of a urea reagent containing 5 mM potassium phosphate, 2000 U/L G-6-PDH and 100 mM D-glucose.

After 48 hours at 20° C., the conventional reagent had failed to regenerate any NADH consumed after reagent contamination with ammonia. Over the same time period, the urea reagent of the invention with 20 mM D-glucose had regenerated 0.23 absorbance units, or 0.04 mM NADH. Over 48 hours, the urea reagent of the invention with 100 mM D-glucose had regenerated 0.70 absorbance units, or 0.11 mM NADH. These results indicate the ability of the reagent described herein to overcome NADH depletion in the urea reagent following reagent contamination with ammonia.

TABLE 12

MAXIMAL RATES OF NADH REGENERATION FOR THE UREA REAGENT AT 20° C. AS MEASURED AT 240 NM.

| Urea Reagent Conditions | Regeneration Rate (m/Abs/min) |
| --- | --- |
| Conventional Reagent | −0.02 |
| Reagent according to invention containing 5 mM Na-$PO_4$ 2000 U/L G-6-PDH and 2 mM D-Glucose | +0.088 |
| Reagent according to invention containing 5 mM K-$PO_4$, 2000 U/L G-6-PDH and 100 mM D-Glucose | +0.386 |

The maximal rates of NADH regeneration in the respective urea reagents is presented in Table 12. In the conventional urea reagent, there was a slow loss in absorbance over time, following the clearance of contaminant ammonia. In the formulation of the invention the rate of NADH regeneration increased with an increase in the concentration of D-glucose in the reagent.

Ammonia reagents were prepared with ingredients as described in Table 6B above, except that the ratio of Tris/TrisHCl buffer (100 mM total buffer) was varied such that reagent pH values were obtained in the range pH 8.0–9.3. A final concentration of 0.2 mM NADPH was also used in the ammonia reagents prepared. A control ammonia reagent was also prepared with no D-glucose, potassium phosphate or G-6-PDH. Reagents were prepared with a level of 0.1 mM ammonia introduced into the reagent system (final concentration) as a contaminant. This level of ammonia contaminant is sufficient to consume 0.1 mM NADPH in the respective reagents—equivalent to 0.62 absorbance units at 340 nm. After reaction completion (i.e., complete clearance of ammonia from the reagents), the absorbance of the various solutions (placed in sealed cuvettes) was monitored over time on a Shimadzu spectrophotometer at 340 nm, and at a temperature of 20° C.

Figure 2:
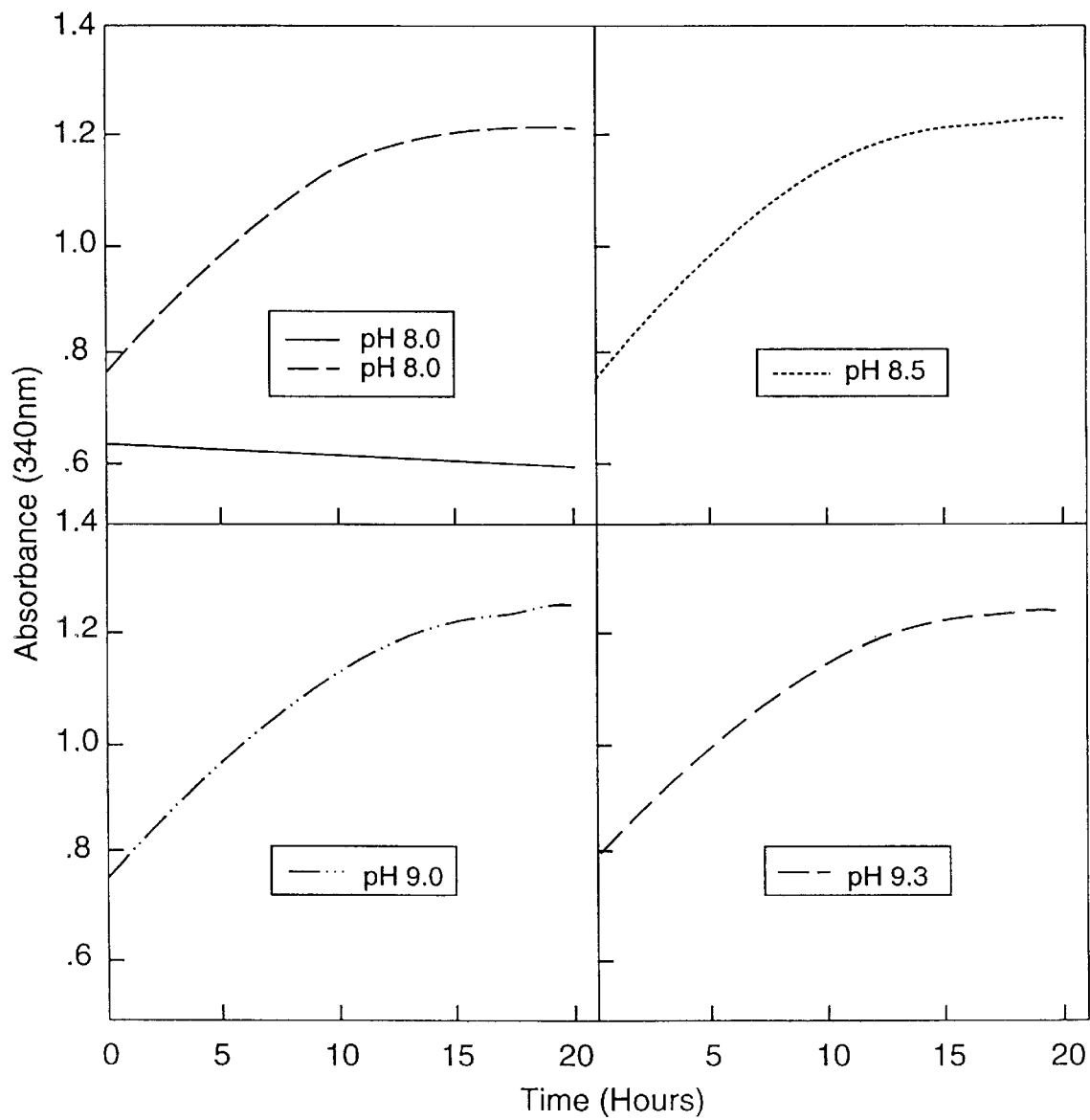

The results presented in FIG. 2 show the time dependent regeneration of NADPH from NADP in ammonia reagent formulations between pH 8.0–9.3 according to the invention after contamination with 0.1 mM ammonia. NADPH regeneration following the clearance of contaminant ammonia was complete within 24 hours of ammonia contamination at 20° C. Maximal rates of NADPH regeneration in the respective ammonia reagents is presented in Table 13. In the conventional ammonia reagent at pH 8.0, the absorbance of the solution remained between 0.6–0.65, with a slow loss in absorbance. In formulations of the invention at all pH values trialed, the rate of NADPH regeneration was fairly similar. The maximal rate of NADPH regeneration was at pH 8.50. These results clearly indicate the ability of the invention described herein to overcome NADPH depletion in the ammonia reagent following reagent contamination with ammonia.

TABLE 13

MAXIMAL RATES OF NADPH REGENERATION FOR THE AMMONIA REAGENT AT 20° C. AS MEASURED AT 340 nm

| Ammonia Reagent Conditions | Regeneration Rate (m/Abs/min) |
| --- | --- |
| pH 8.0, conventional Reagent | −0.03 |
| pH 8.0, invention formulation | +0.78 |
| pH 8.5, invention formulation | +0.85 |
| pH 9.0, invention formulation | +0.76 |
| pH 9.3, invention formulation | +0.71 |

EXAMPLE 3

Rates of Loss of NAD(P)H in Ammonia and Urea Reagents

A Urea Reagent

Urea reagents were prepared with a formulation composition as described in Table 5B, with the following variations. The final concentration of NADH in the reagent formulations was 0.25 mM. Urea reagent pH was adjusted by variation of the ratio of Tris/TrisHCl (100 mM buffer total). Control Urea reagent solutions were prepared in the absence of D-glucose, phosphate and G-6-PDH.

The absorbance of sample solutions of the reagents, stored in sealed cuvettes at 20±2° C., was monitored at 340 nm.

The decrease in absorbance of urea reagent solutions over time on storage at 20±2° C., as monitored at 340 nm, is presented in Table 14. It is apparent that both in the presence and absence of the inventive coenzyme regeneration system, solutions lose absorbance more rapidly at pH 8.0 than at pH 8.5. In the formulation of the invention, however, the rate of reagent solution absorbance loss was also significantly less rapid. In other words, elevated pH and the incorporation of the inventive coenzyme regeneration system significantly reduces the rate of disappearance of NADPH from the urea reagent solution.

It should be noted that while a rise in pH above 8.5 will also promote the stability of NADH, commercially available urease and glutamate dehydrogenase enzymes become increasingly less stable and less active in the reagent formulation. Consequently, a balance is required in reagent formulation pH, such that adequate enzyme activity and stability is maintained, while also providing reasonable NADH stability. On this basis, a reagent formulation of approximately pH 8.5 is preferred.

TABLE 14

ABSORBANCE (340 NM) OF UREA REAGENT SOLUTIONS STORED AT 20° C. AS A FUNCTION OF TIME

| Incubation Period (days) | pH 8.0 conventional formulation | pH 8.0 inventive formulation | pH 8.5 conventional formulation | pH 8.5 inventive formulation |
| --- | --- | --- | --- | --- |
| 0 | 1.73 | 1.72 | 1.77 | 1.74 |
| 7 | 1.63 | 1.68 | 1.7 | 1.75 |
| 14 | 1.52 | 1.61 | 1.64 | 1.7 |
| 23 | 1.36 | 1.48 | 1.54 | 1.62 |
| 29 | 1.25 | 1.4 | 1.47 | 1.53 |
| 37 | 1.12 | 1.3 | 1.38 | 1.52 |

B Ammonia Reagent

Ammonia reagents were prepared with a formulation composition as described in Table 6B with the following variations. Ammonia reagent pH was adjusted by variation of the ratio of Tris/TrisHCl (100 mM buffer total). The final concentration of NADPH in the Ammonia reagent solutions was 0.2 mM. Control Ammonia reagent solutions were prepared without D-glucose, phosphate and G-6-PDH.

The absorbance of sample solutions of the reagents, stored in sealed cuvettes at 20±2° C., was monitored at 340 nm.

The decrease in absorbance of ammonia reagent solutions over time on storage at 20° C., as monitored at 340 nm, is presented in Table 15. It is apparent that both in the presence and absence of the inventive coenzyme regeneration system solutions lose absorbance more rapidly with a reduction in pH. In formulations of the present invention, however, the rate of reagent solution absorbance loss was also significantly less rapid. In other words, elevated pH and the incorporation of the coenzyme regeneration system significantly reduces the rate of disappearance of NADPH form the ammonia reagent solution.

It should be noted that while a rise in pH will promote the stability of NADPH, commercially available glutamate dehydrogenase becomes increasingly less stable and less active in the reagent formulation above pH 8.5. Consequently, a balance is required in reagent formulation pH, such that adequate enzyme activity and stability is maintained, while also providing reasonable NADPH stability. On this basis, a reagent formulation of pH 8.5–9.0 is preferred.

TABLE 15

ABSORBANCE (340 nm) OF AMMONIA REAGENT SOLUTIONS STORED AT 20° C. AS A FUNCTION OF TIME

| incubation Period (days) | pH 8.0 conventional formulation | pH 8.0 with Regen. Technology inventive formulation | pH 8.5 conventional formulation | pH 8.5 with Regen. Technology inventive formulation | pH 9.0 conventional formulation | pH 9.0 with Regen. Technology inventive formulation |
| --- | --- | --- | --- | --- | --- | --- |
| 0 | 1.39 | 1.41 | 1.38 | 1.41 | 1.4 | 1.41 |
| 6 | 1 | 1.09 | 1.2 | 1.27 | 1.31 | 1.36 |
| 12.9 | 0.64 | 0.79 | 0.99 | 1.12 | 1.2 | 1.29 |
| 20.1 | 0.39 | 0.57 | 0.79 | 0.97 | 1.09 | 1.22 |
| 32.9 | 0.15 | 0.33 | 0.49 | 0.74 | 0.87 | 1.07 |
| 38.1 | 0.13 | 0.28 | 0.39 | 0.67 | 0.8 | 1.03 |

EXAMPLE 4

Functionality of Ammonia and Urea Reagents

A Urea Reagents

The urea reagent was prepared according to the ingredient listing in Table 5B, in the presence and absence of D-glucose, phosphate and G-6-PDH. However, the final concentration of NADH in the reagent formulations was 0.25 mM. Linearity of the reagents was compared against Verichem/Normal/Abnormal controls, on a ROCHE® COBAS MIRA™ instrument, using the parameters specified below.

Reaction Temperature: 37° C.

Sample to reagent volume: 1:100

Wavelength: 340 nm

The results presented in Table 16 indicate that the urea reagent at pH 8.50 of the present invention, is linear up to the highest level of urea control sample tested (Verichem level E, with 37.4 mM urea), with the measured values variation within 5% of the specified concentration. The urea reagent of the invention also faithfully reads within the deviation of the value for normal and abnormal urea control samples.

TABLE 16

LINEARITY STUDIES WITH THE UREA REAGENT AT PH 8.50

| Control Sample | Specified Urea Concentration for Control Samples (mM) | Estimated Urea Concentration for Control Samples (mM) | |
|---|---|---|---|
| | | Urea reagent of invention | Urea reagent (conventional) |
| Verichem level A | 1.8 | 2 | 2 |
| Verichem level B | 10.7 | 10.8 | 11.3 |
| Verichem level C | 19.6 | 19.9 | 19.6 |
| Verichem level D | 28.5 | 27.7 | 26.7 |
| Verichem level E | 37.4 | 35.9 | 35.8 |
| Normal Control | 5.2 ± 1.4 | 5.2 | 5.2 |
| Abnormal Control | 18.3 ± 2.1 | 19.1 | 18.6 |

B Ammonia Reagent

The ammonia reagent was prepared in the presence and absence of D-glucose, phosphate and G-6-PDH according to the ingredient listing in Table 6B. Linearity of the reagents was compared against aqueous ammonia controls, on a ROCHE®COBAS MIRA™ instrument, using the parameters specified below.

Reaction Temperature: 37° C.

Sample to reagent volume: 1:10

Wavelength: 340 nm

The results presented in Table 17 indicate that the ammonia reagent at pH 8.50 of the invention is linear up to the highest level of ammonia control sample tested (1200 $\mu$M ammonia), with the measured values variation within 5% of the specified concentration

TABLE 17

LINEARITY STUDIES WITH THE AMMONIA REAGENT AT pH 8.50

| Specified Ammonia Concentration for Aqueous Control Sample ($\mu$M) | Mean Estimated Ammonia Concentration for Control Samples ($\mu$M), from Duplicate Measurements |
|---|---|
| 10 | 11.6 ± 6 |
| 20 | 24.2 ± 2.3 |
| 50 | 52.5 ± 3.1 |
| 100 | 101.9 ± 2.7 |

TABLE 17-continued

LINEARITY STUDIES WITH THE AMMONIA REAGENT AT pH 8.50

| Specified Ammonia Concentration for Aqueous Control Sample ($\mu$M) | Mean Estimated Ammonia Concentration for Control Samples ($\mu$M), from Duplicate Measurements |
|---|---|
| 200 | 203.5 ± 1.3 |
| 400 | 409.7 ± 3.1 |
| 800 | 789.3 ± 3.5 |
| 1200 | 1164 ± 2.2 |

EXAMPLE 5

The urea reagent can be configured in a two vial format, according to the formulation configuration specified below. The relative volume of addition of vial A and vial B reagent required to obtain the combined reagent is 5:1 for vial A:vial B.

Urea Vial A

| Raw Material | Molecular Weight | Concentration | Quantity/Liter |
|---|---|---|---|
| TRIS | 121.14 | 61.3 mM | 7.43 g |
| TRIS-HCl | 157.6 | 38.7 mM | 6.10 g |
| NADH, Na$_2$.3H$_2$O | 763.5 | 0.34 mM | 0.26 g |
| NaN$_3$ | 65.01 | 7.7 mM | 0.5 g |
| K$_2$HPO$_4$ | 174.18 | 5 mM | 0.871 g |
| D-Glucose | 180.16 | 100 mM | 18.02 g |
| BSA | — | 0.05% | 0.5 g |
| G-6-PDH, Leucononstoc mesenteroides | | 2000 U/L | 2000 U |

Urea Vial B

| Raw Material | Molecular Weight | Concentration | Quantity/Liter |
|---|---|---|---|
| TRIS | 121.14 | 61.3 mM | 7.43 g |
| TRIS-HCl | 157.6 | 38.7 mM | 6.10 g |
| α-Ketoglutarate, Na salt (anhydrous) | 190.1 | 45 mM | 8.55 g |
| EDTA, Na$_2$.3H$_3$O | 372.24 | 1 mM | 0.372 g |
| BSA | — | 0.05% | 0.5 g |
| GLDH (microbial) | — | 50000 U/L | 50000 U |
| Urease (microbial) | — | 40000 U/L | 40000 U |

Ammonia Reagent, 2 Vial Format

The ammonia reagent can be configured in a two vial format, according to the formulation configuration specified below. The relative volume of addition of vial A and B reagent required to obtain the combined reagent is 5:1 for vial A:vial B. In the example formulation provided, NADH is used instead of NADPH. As a consequence, LDH is included in vial A for the removal of interferent patient sampe pyruvate prior to the commencement of the main assay reaction.

Ammonia Vial A

| Raw Material | Molecular Weight | Concentration | Quantity/Liter |
|---|---|---|---|
| TRIS | 121.14 | 61.3 mM | 7.43 g |
| TRIS-HCl | 157.6 | 38.7 mM | 6.10 g |
| NADH, Na$_2$.3H$_2$O | 763.5 | 0.34 mM | 0.26 g |
| NaN$_3$ | 65.01 | 7.7 mM | 0.5 g |

-continued

Ammonia Vial A

| Raw Material | Molecular Weight | Concentration | Quantity/Liter |
|---|---|---|---|
| $K_2HPO_4$ | 174.18 | 5 mM | 0.871 g |
| D-Glucose | 180.16 | 100 mM | 18.02 g |
| BSA | — | 0.05% | 0.5 g |
| G-6-PDH, Leucononstoc mesenteroides | | 2000 U/L | 2000 U |
| LDH (microbial) | — | 2000 U/L | 2000 U |

Ammonia Vial B

| Raw Material | Molecular Weight | Concentration | Quantity/Liter |
|---|---|---|---|
| TRIS | 121.14 | 61.3 mM | 7.43 g |
| TRIS-HCl | 157.6 | 38.7 mM | 6.10 g |
| α-Ketoglutarate, Na salt (anhydrous) | 190.1 | 45 mM | 8.55 g |
| EDTA, $Na_2.3H_2O$ | 372.24 | 1 mM | 0.372 g |
| BSA | — | 0.05% | 0.5 g |
| GLDH (microbial) | — | 50000 U/L | 50000 U |
| Urease (microbial) | — | 40000 U/L | 40000 U |

Other major advantages of the reagent and method according to the invention are that the reagent is in its most preferred form, a single vial reagent thereby reducing space and inventory problems associated with prior art reagents, and that it is adaptable to varying instrumentation systems.

It should be appreciated that there are numerous substrate/enzyme "non-specific" pairs which may be used to slow the regeneration of the coenzyme used in the reagent and method of the invention. In addition to those mentioned herein, there are others which are not commercially available or which are prohibitively expensive.

It will also be appreciated that this invention will be applicable to the stabilization of reagents other than AST, ALT, ammonia and urea, for example, LDH (pyruvate to lactate), triglyceride and salicylate. The invention should not be considered limited by the exemplification thereof in this specification with reference specifically to AST, ALT, ammonia and urea.

We claim:

1. A reagent for the determination of an analyte concentration in a patient wherein the degree of oxidation of a coenzyme is measured, characterized in that said reagent is stabilized against oxidation by a coenzyme reduction system comprising an enzyme and a substrate pair selected so as to enable continuous regeneration of said coenzyme throughout storage of said reagent, said enzyme having incomplete specificity for said substrate such that there is no loss in functionality of the reagent in the determination of analyte concentration throughout at least 6–8 months of storage of said reagent at 2°–8° C.

2. The reagent of claim 1 which is configured as a single vial.

3. The reagent of claim 1 wherein said continuous regeneration occurs at a rate in the range of 0.01 to 0.9 mAbs/min at 18° to 25° C.

4. The reagent of claim 1 wherein said enzyme is derived from a microbial source.

5. The reagent of claim 1 wherein said enzyme/substrate pair is glucose-6-phosphate dehydrogenase/D-glucose.

6. The reagent of claim 1 wherein the degree of specificity between said enzyme and said substrate is less than 50% on an equimolar basis.

7. The reagent of claim 6 wherein the degree of specificity between said enzyme and said substrate is less than 10% on an equimolar basis.

8. The reagent of claim 1 wherein said analyte is a transaminase.

9. The reagent of claim 8 wherein said transaminase is aspartate transaminase.

10. The reagent of claim 8 wherein said transaminase is alanine transaminase.

11. The reagent of claim 1 wherein said analyte is urea.

12. The reagent of claim 1 wherein said analyte is ammonia.

13. A reagent for enzymatic determination of an analyte concentration in a patient wherein the degree of oxidation of a coenzyme is measured characterized in that said reagent is configured as a single vial and is stabilized against oxidation by a coenzyme reduction system comprising an enzyme and substrate pair selected so as to enable continuous regeneration of a coenzyme throughout storage of said reagent such that there is no loss in functionality of the reagent in the determination of analyte concentration throughout at least 6–8 months of storage of said reagent at 2°–8° C.

14. The reagent claim 13 wherein said coenzyme reduced system comprises an enzyme and a substrate, said enzyme having incomplete specificity for said substrate.

15. The reagent of claim 13 wherein said continuous regeneration occurs at a rate in the range of 0.01 to 0.9 mAbs/min at 18° to 25° C.

16. The reagent of claim 13 wherein said enzyme is derived from a microbial source.

17. The reagent of claim 13 wherein said enzyme/substrate pair is glucose-6-phosphate dehydrogenase/D-glucose.

18. The reagent of claim 13 wherein the degree of specificity between said enzyme and said substrate is less than 50% on an equimolar basis.

19. The reagent of claim 13 wherein the degree of specificity between said enzyme and said substrate is less than 10% on an equimolar basis.

20. The reagent as claimed in claim 13 wherein said analyte is a transaminase.

21. The reagent as claimed in claim 20 wherein said transaminase is aspartate transaminase.

22. The reagent of claim 20 wherein said transaminase is alanine transaminase.

23. The reagent as claimed in claim 13 wherein said analyte is urea.

24. The reagent as claimed in claim 13 wherein said analyte is ammonia.

25. An improvement in an enzymatic method of determination of an analyte concentration in a sample body fluid wherein the degree of oxidation of a coenzyme is measured, the improvement comprising stabilizing a reagent comprising said coenzyme against oxidation by a coenzyme reduction system comprising an enzyme and substrate pair selected so as to enable continuous regeneration of said coenzyme throughout storage of said reagent, said enzyme having incomplete specificity for said substrate such that there is no loss in functionality of the reagent in the determination of analyte concentration throughout at least 6–8 months of storage of said reagent at 2°–8° C.

26. The improvement of claim 25 in which the reagent is configured as a single vial.

27. The improvement of claim 25 wherein said continuous regeneration occurs at a rate in the range of 0.01 to 0.9 mAbs/min at 18° to 25° C.

28. The improvement of claim 25 in which said enzyme is derived from a microbial source.

29. The improvement of claim 25 wherein said enzyme/substrate pair is glucose-6-phosphate dehydrogenase/D-glucose.

30. The improvement of claim 25 wherein the degree of specificity between said enzyme and said substrate is less than 50% on an equimolar basis.

31. The improvement of claim 30 wherein the degree of specificity between said enzyme and said substrate is less than 10% on an equimolar basis.

32. The improvement of claim 25 wherein said analyte is transaminase.

33. The improvement of claim 32 wherein said analyte is aspartate transaminase.

34. The improvement of claim 32 wherein said analyte is alanine transaminase.

35. The improvement of claim 25 wherein said analyte is urea.

36. The improvement of claim 25 wherein said analyte is ammonia.

* * * * *